United States Patent [19]
Rosini et al.

[11] Patent Number: 5,330,981
[45] Date of Patent: Jul. 19, 1994

[54] ARYLALKYL ESTERS OF 4,5-DIHYDROXY-9,10-DIHYDRO-9,10-DIOXO-2-ANTHRACENECARBOXYLIC ACID HAVING THERAPEUTICAL ACTIVITY

[75] Inventors: Sergio Rosini; Maurizio Mian, both of Pisa, Italy

[73] Assignee: Istituto Gentili S.p.A., Pisa, Italy

[21] Appl. No.: 966,038

[22] PCT Filed: Apr. 21, 1992

[86] PCT No.: PCT/EP92/00881
§ 371 Date: Dec. 30, 1992
§ 102(e) Date: Dec. 30, 1992

[87] PCT Pub. No.: WO92/19584
PCT Pub. Date: Nov. 12, 1992

[30] Foreign Application Priority Data

May 3, 1991 [IT] Italy .................. MI91 A 001215

[51] Int. Cl.5 .................. A61K 31/60; A61K 31/44; A61K 31/40; A61K 31/215

[52] U.S. Cl. .................. 514/159; 514/224.8; 514/291; 514/352; 514/374; 514/375; 514/411; 514/416; 514/419; 514/420; 514/423; 514/427; 514/429; 514/448; 514/507; 514/510; 544/35; 546/310; 549/70; 549/89; 548/224; 548/235; 548/427; 548/432; 548/444; 548/486; 548/490; 548/494; 548/539; 548/562; 548/565; 552/262

[58] Field of Search .................. 552/262; 514/510, 411, 514/374, 224.8, 429, 291, 448, 352, 419, 420, 427, 416, 423, 507, 159, 375; 548/444, 432, 235, 565, 490, 494, 562, 486, 427, 539, 224; 544/35; 549/89, 70; 546/310

[56] References Cited

PUBLICATIONS

Morrison & Boyd, *Organic Chemistry*, 4th Ed., (1983), pp. 827–828, 831, 820–825, 837–838.

Primary Examiner—Johann Richter
Assistant Examiner—Kimberly J. Kestler
Attorney, Agent, or Firm—Bucknam and Archer

[57] ABSTRACT

This application describes 3-arylalkyl esters of 4,5-dihydro-9,10-dioxo-2-anthracenecarboxylic acid and a process for making them. Also described is a method of using the compounds in the treatment of arthritis.

11 Claims, No Drawings

ARYLALKYL ESTERS OF 4,5-DIHYDROXY-9,10-DIHYDRO-9,10-DIOXO-2-ANTHRACENECARBOXYLIC ACID HAVING THERAPEUTICAL ACTIVITY

The present invention relates to arylalkyl esters of 4,5-dihydroxy-9,10-dihydro-9,10-dioxo-2-anthracenecarboxylic acid of general formula:

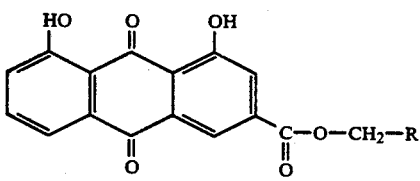

wherein $R-CH_2-O-$ is the residue of an $R-CH_2OH$ alcohol deriving from the reduction of an $R-COOH$ carboxylic acid having antiinflammatory action, which belongs in the class of salicylic, arylacetic, arylpropionic, anthranylic acids.

Examples of antiinflammatory acids are reported hereinbelow: salicylic acids: salicylic acid, acetylsalicylic acid, 5-aminosalicylic acid, diflunisal, fendosal; arylacetic acids: acemetacin, alclofenac, amfenac, benzadac, bufexamac, bumadizone, cinmetacin, clidanac, clometacin, clopirac, diclofenac, etodolac, fenclofenac, indobufen, indometacin, methiazinic acid, sulindac, tolmetin, zomepirac; propionic acids: alminoprofen, benoxaprofen, bucloxic acid, carprofen, flurbiprofen, ibuprofen, ketoprofen, loxoprofen, naproxen, oxaprozin, protizinic acid, pineprofen, pirprofen, pranofropen, suprofen, thiaprofenic acid; anthranilic acids: flufenamic acid, meclofenamic acid, mefenamic acid, niflumic acid, lobenzarit, tolfenamic acid.

Particularly preferred are the compounds of formula (I) wherein R is, according to the above definition, a residue from the following compounds: acid salicylic, acid acetylsalicylic, diflunisal, ibufenac, ibuprofen, naproxen, indometacin.

The present invention also relates to the compounds of formula (I) wherein the hydroxy groups at the 4,5-positions of the anthracenedione ring and any hydroxy groups present on the aryl moiety of the R residue are esterified with lower aliphatic acids. The present invention further relates to the compounds of formula (I) in which any amino groups present in the R residues are acetylated or, if possible, salified.

The compounds of formula (I) are prepared by reacting 4,5-di(acetyloxy)-9,10-dihydro-9,10-dioxo-2-anthracenecarboxylic acid chloride of formula (II)

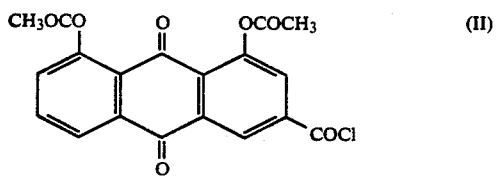

with a primary alcohol $R-CH_2OH$ in which R is as defined above.

The acid chloride (II) can be replaced by any reactive derivative of said acid (such as the ester, mixed anhydride, and the like); or the acid can directly be reacted with an alcohol $R-CH_2OH$ in the presence of dicyclohexylcarbodiimide and the like.

The esterification reaction is carried out in an inert solvent, such as chloroform, in the presence of an acid-binding agent, for example triethylamine.

The resulting ester is treated with aqueous ammonia, preferably 10% ammonia, in order to deacetylate the hydroxy groups at the 4- and 5-positions of the anthracene ring, to give a compound of formula (I) wherein said hydroxy groups are free.

The compounds of the invention have interesting pharmacological properties, which are higher than those predictable by the mere addition of compounds having antiinflammatory activity with the (4,5-dihydroxy-9,10-dihydro-9,10-dioxo-2-anthracenecarboxylic acid) molecule, which is already used in the osteoarthritis therapy.

The advantageous pharmacological properties of the compounds of the invention make them useful as such or in form of pharmaceutically acceptable salts (or esters) thereof for the preparation of medicaments, in admixture with appropriate conventional carriers. Examples of pharmaceutical compositions are tablets, capsules, pills, injectable solutions or suspensions, ointments, creams and the like. Doses will range from 5 to 500 mg for unit dose, the daily dose depending on the severity of the condition to treat as well as on the general conditions of the patient.

The following examples further illustrate the invention.

EXAMPLE 1

2-Hydroxybenzyl 4,5-dihydroxy-9,10-dihydro-9,10-dioxo-2-anthracenecarboxylate

A solution of 1.55 g (12.5 mmoles) of 2-hydroxybenzyl alcohol in 20 ml of anhydrous chloroform, cooled in ice-bath, is added with 1.66 ml (12 mmoles) of anhydrous triethylamine. A solution of 4.7 g (12 mmoles) of 4,5-acetoxy-9,10-dihydro-9,10-dioxo-2-anthracenecarboxylic acid chloride in 80 ml of anhydrous chloroform is added to the stirred solution, with cooling. The reaction mixture is left to react at room temperature for 4 hours. After that, chloroform is evaporated off under reduced pressure and the residue is kept under magnetic stirring overnight in a sodium bicarbonate saturated solution. Thereafter, the mixture is extracted with chloroform, solvent is evaporated off under reduced pressure and the crude residue is stirred for a night in 60 ml of a 10% $NH_3$ aqueous solution. The mixture is acidified with conc. HCl to pH 5 and extracted with chloroform, which is then evaporated under reduced pressure and the crude residue containing the title product is purified by means of silica gel chromatography with a 3:7 ethyl acetate/cyclohexane mixture. M.p. 125°-130° C.

IR and $^1H$ NMR in agreement. Elementary analysis for $C_{22}H_{14}O_7$:

| | Calculated % | Found % |
| --- | --- | --- |
| C | 67.69 | 67.61 |
| H | 3.61 | 3.57 |
| O | 28.69 | 28.73 |

EXAMPLE 2

5-(2,4-Difluorophenyl)-2-hydroxybenzyl 4,5-dihydroxy-9,10-dihydro-9,10-dioxo-2-anthracenecarboxylate The procedure of example 1 is repeated, but using 2.95 g (12.5 mmoles) of 5-(2,4-difluorophenyl)-2-hydroxybenzyl alcohol. The title product is obtained which is purified by silica gel chromatography with a 2:8 ethyl acetate/cyclohexane mixture. M.p. 128°–132° C.

IR and $^1$H NMR in agreement. Elementary analysis for $C_{28}H_{16}F_2O_7$:

|   | Calculated % | Found % |
|---|---|---|
| C | 66.93 | 66.85 |
| H | 3.21  | 3.16  |
| O | 22.29 | 22.21 |

EXAMPLE 3

2-(4-Isobutylphenyl)-ethyl 4,5-dihydroxy-9,10-dihydro-9,10-dioxo-2-anthracenecarboxylate The procedure of example 1 is repeated, but using 2.14 g (12 mmoles) of 2-(4-isobutylphenyl)-ethyl alcohol. The title product is obtained which is purified by silica gel chromatography with a 1:9 ethyl acetate/cyclohexane mixture. M.p. 117°–121° C.

IR and $^1$H NMR in agreement. Elementary analysis for $C_{27}H_{24}O_6$:

|   | Calculated % | Found % |
|---|---|---|
| C | 72.95 | 73.06 |
| H | 5.44  | 5.49  |
| O | 21.80 | 21.52 |

EXAMPLE 4

2-(4-Isobutylphenyl)-propyl 4,5-dihydroxy-9,10-dihydro-9,10-dioxo-2-anthracenecarboxylate The procedure of example 1 is repeated, but using 2.3 g (12 mmoles) of 2-(4-isobutylphenyl)-propyl alcohol. The title product is obtained which is purified by silica gel chromatography with a 1:9 ethyl acetate/cyclohexane mixture. M.p. 115° C.

IR and $^1$H NMR in agreement. Elementary analysis for $C_{28}H_{26}O_6$:

|   | Calculated % | Found % |
|---|---|---|
| C | 73.34 | 73.28 |
| H | 5.71  | 5.66  |
| O | 20.93 | 20.86 |

EXAMPLE 5

2-(6-Methoxy-2-naphthyl)-propyl 4,5-dihydroxy-9,10-dihydro-9,10-dioxo-2-anthracenecarboxylate The procedure of example 1 is repeated, but using 2.6 g (12 mmoles) of 2-(6-methoxy-2-naphthyl)-propyl alcohol. The title product is obtained which is purified by silica gel chromatography with a 4:6 ethyl acetate/cyclohexane mixture. M.p. 147°–151° C.

IR and $^1$H NMR in agreement. Elementary analysis for $C_{29}H_{22}O_7$:

|   | Calculated % | Found % |
|---|---|---|
| C | 72.19 | 72.26 |
| H | 4.59  | 4.63  |
| O | 23.21 | 23.29 |

EXAMPLE 6

2-[1-(4-Chlorobenzoyl)-2-methyl-5-methoxy-1H-indol-3-yl]-ethyl 4,5-dihydroxy-9,10-dihydro-9,10-dioxo-2-anthracenecarboxylate The procedure of example 1 is repeated, but using 3.95 g (12 mmoles) of 2-[1-(4-chlorobenzoyl)-2-methyl-5-methoxy-H-indol-3-yl]-ethy alcohol. The title product is obtained which is purified by silica gel chromatography with a 3:7 ethyl acetate/cyclohexane mixture. M.p. 139°–146° C.

IR and $^1$H NMR in agreement. Elementary analysis for $C_{34}H_{24}ClO_8$:

|   | Calculated % | Found % |
|---|---|---|
| C | 68.50 | 68.41 |
| H | 4.05  | 4.00  |
| O | 21.47 | 21.42 |

We claim:

1. A compound of formula (1)

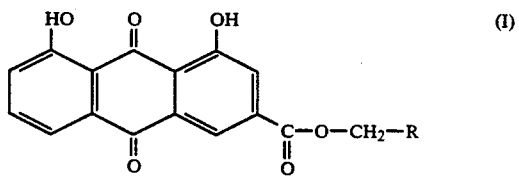

wherein R—CH$_2$—O— is the residue of an R—CH$_2$OH alcohol derived from the reduction of an R—COOH carboxylic acid having anti-inflammatory action, which is a member selected from the group consisting of salicylic, arylacetic, arylpropionic, and anthranilic acids; or enantiomers, diastereoisomers and mixtures thereof or pharmaceutically acceptable salts thereof.

2. A compound according to claim 1 wherein the R—CH$_2$—O— residue is derived from one of the following compounds:

1) salicylic acid acetylsalicylic acid, 5-aminosalicylic acid, diflunisal, fendosal;
2) acemetacin, alclofenac, amfenac, benzadac, bufexamac, bumadizone, cinmetacin, clidanac, clometacin, clopirac, diclofenac, etodolac, fenclofenac, indobufen, indometacin, methiazinic acid, sulindac, tolmetin, zomepirac;
3) alminoprofen, benoxaprofen, bucloxic acid, carprofen, flurbiprofen, ibuprofen, ketoprofen, loxoprofen, naproxen, oxaprozin, protizinic acid, pineprofen, pirprofen, pranoprofen, suprofen, thiaprofenic acid;
4) flufenamic acid, meclofenamic acid, mefenamic acid, niflumic acid, lobenzarit or tolfenamic acid.

3. A compound according to claim 2, wherein the R—CH$_2$—O— residue is derived from a member selected from the group consisting of: salicylic acid, diflunisal, ibufenac, ibuprofen, naproxen and indometacin.

4. A pharmaceutical composition in unit dosage form containing 5-500 mgs per unit dose of a compound according to claim 1 as the active ingredient in admixture with pharmaceutically acceptable carriers and excipients.

5. A compound according to claim 1 which is 2-hydroxybenzyl 4,5-dihydroxy-9,10-dihydro-9,10-dioxo-2-anthracenecarboxylate.

6. A compound according to claim 1 which is 5-(2,4-difluorophenyl)-2-hydroxybenzyl 4,5-dihydroxy-9,10-dihydro-9,10 dioxo-2-anthracenecarboxylate.

7. A compound according to claim 1 which is 2-(4-Isobutylphenyl)-ethyl 4,5-dihydroxy-9,10-dihydro-9,10-dioxo-2-anthracenecarboxylate.

8. A compound according to claim 1 which is 2-(4-Isobutylphenyl)-propyl 4,5-dihydroxy-9,10-dihydro-9,10-dioxo-2-anthracenecarboxylate.

9. A compound according to claim 1 which is 2-(6-Methoxy-2-naphthyl)-propyl) 4,5-dihydroxy-9,10-dihydro-9,10-dioxo-2-anthracenecarboxylate.

10. A compound according to claim 1 which is 2-[1-(4-Chlorobenzoyl)-2-methyl-5-methoxy-1H-indol-3-yl]-ethyl 4,5-dihydroxy-9,10-dihydro-9,10-dioxo-2-anthracenecarboxylate.

11. The method of treatment of a living subject affected by arthritis which consists of administering to said subject an effective amount of a composition containing as the active ingredient a compound of formula (1)

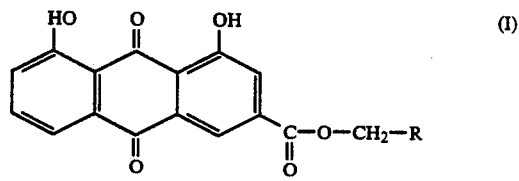

wherein R—CH$_2$—O— is the residue of an R—CH$_2$OH alcohol derived from the reduction of an R—COOH carboxylic acid having anti-inflammatory action, which is a member selected from the group consisting of salicylic, arylacetic, arylpropionic, and anthranilic acids; or enantiomers, diastereoisomers and mixtures thereof or pharmaceutically acceptable salts thereof.

* * * * *